United States Patent
Karicherla et al.

(10) Patent No.: US 12,089,938 B2
(45) Date of Patent: Sep. 17, 2024

(54) ALTERED MATERIAL MORPHOLOGY FOR REDUCING FIBROTIC LOAD, REDUCING NOISE AND IMPROVING EXTRACTABILITY OF IMPLANTABLE LEADS

(71) Applicant: Verily Life Sciences LLC, South San Francisco, CA (US)

(72) Inventors: Annapurna Karicherla, South San Francisco, CA (US); Bejamin K. Yaffe, South San Francisco, CA (US); Celine Liong, San Mateo, CA (US); Kimberly Kam, Orinda, CA (US)

(73) Assignee: Verily Life Sciences LLC, South San Francisco, CA (US)

( * ) Notice: Subject to any disclaimer, the term of this patent is extended or adjusted under 35 U.S.C. 154(b) by 791 days.

(21) Appl. No.: 17/267,908

(22) PCT Filed: Aug. 1, 2019

(86) PCT No.: PCT/US2019/044636
§ 371 (c)(1),
(2) Date: Feb. 11, 2021

(87) PCT Pub. No.: WO2020/036743
PCT Pub. Date: Feb. 20, 2020

(65) Prior Publication Data
US 2021/0244331 A1    Aug. 12, 2021

Related U.S. Application Data

(60) Provisional application No. 62/718,619, filed on Aug. 14, 2018.

(51) Int. Cl.
*A61B 5/263*    (2021.01)
*A61B 5/294*    (2021.01)
(Continued)

(52) U.S. Cl.
CPC .............. *A61B 5/263* (2021.01); *A61B 5/388* (2021.01); *A61N 1/05* (2013.01); *A61B 5/294* (2021.01);
(Continued)

(58) Field of Classification Search
CPC . A61B 5/263; A61B 5/294; A61B 2562/0209; A61B 2562/028;
(Continued)

(56) References Cited

U.S. PATENT DOCUMENTS 7,689,260 B2    3/2010  Finch et al.
8,005,526 B2    8/2011  Martin et al.
(Continued)

OTHER PUBLICATIONS

U.S. Appl. No. 16/394,558 , Non-Final Office Action, Mailed on Nov. 2, 2020, 9 pages.
(Continued)

*Primary Examiner* — Linda C Dvorak
*Assistant Examiner* — Abigail Bock
(74) *Attorney, Agent, or Firm* — Kilpatrick Townsend & Stockton LLP

(57) ABSTRACT

Embodiments relate to implantable-lead devices that include one or more materials with altered morphology and methods for making and using the same. Specifically, the morphology of electrodes and/or one or more other implant-device materials can be textured to include micro- and/or nanoscale topographical features, which can reduce in vivo fibrotic response and thereby improve signal-to-noise ratios and short-term extractability of the devices.

19 Claims, 6 Drawing Sheets

(51) Int. Cl.
*A61B 5/388* (2021.01)
*A61N 1/05* (2006.01)

(52) U.S. Cl.
CPC . *A61B 2562/0209* (2013.01); *A61B 2562/028* (2013.01); *A61B 2562/0285* (2013.01); *A61B 2562/04* (2013.01); *A61B 2562/125* (2013.01); *A61N 1/0556* (2013.01)

(58) Field of Classification Search
CPC .............. A61B 2562/04; A61B 2562/125; A61N 1/05; A61N 1/0556
See application file for complete search history.

(56) References Cited

U.S. PATENT DOCUMENTS

| | | | | |
|---|---|---|---|---|
| 2001/0029395 | A1* | 10/2001 | Stewart | A61N 1/05 607/116 |
| 2003/0123215 | A1 | 7/2003 | Allen et al. | |
| 2009/0050487 | A1* | 2/2009 | Fang | C25D 1/00 205/135 |
| 2009/0093879 | A1* | 4/2009 | Wawro | A61F 2/0077 623/11.11 |
| 2010/0126404 | A1* | 5/2010 | Brennan | B08B 17/065 114/222 |
| 2011/0301665 | A1 | 12/2011 | Mercanzini et al. | |
| 2014/0293384 | A1 | 10/2014 | O'keeffe et al. | |
| 2015/0174396 | A1 | 6/2015 | Fisher et al. | |
| 2018/0133457 | A1* | 5/2018 | Yao | A61N 1/05 |

OTHER PUBLICATIONS

U.S. Appl. No. 16/394,558, Notice of Allowance, Mailed on Jan. 14, 2021, 5 pages.
Green et al., "Laser patterning of platinum electrodes for safe neurostimulation", Journal of Neural Engineering, vol. 11, No. 5, Sep. 4, 2014.
Ison et al., "Platinum and platinum/iridium electrode properties when used for extracochlear electrical stimulation of the totally deaf", Medical and Biological Engineering and Computing, vol. 25, Issue 4, Jul. 1987, pp. 403-413.
Application No. PCT/US2019/044636, International Search Report and Written Opinion, Mailed on Oct. 25, 2019, 13 pages.
Petrossians et al., "Improved Electrode Material for Deep Brain Stimulation", Proceedings of the 38th Annual International Conference of the IEEE Engineering in Medicine and Biology Society (EMBC), Aug. 16-20, 2016, pp. 1798-1801.
Petrossians et al., "Surface Modification of Neural Stimulating/Recording Electrodes with High Surface Area Platinum-Iridium Alloy Coatings", Proceedings of the Annual International Conference of the IEEE Engineering in Medicine and Biology Society, Aug. 30-Sep. 3, 2011, pp. 3001-3004.

* cited by examiner

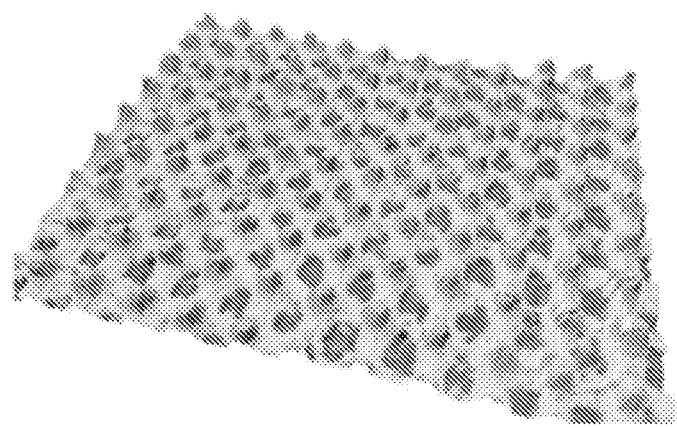
FIG. 3A
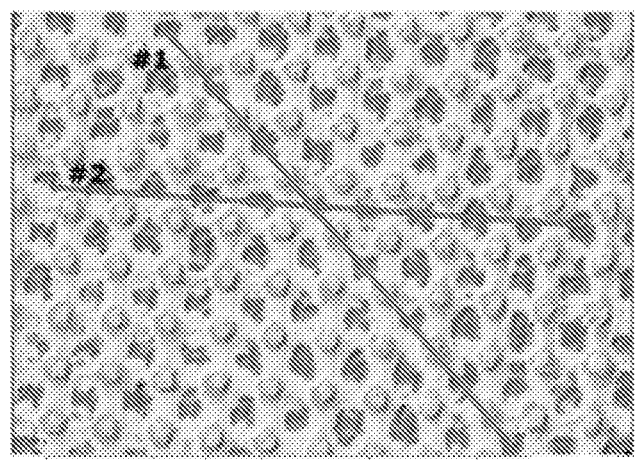
FIG. 3B
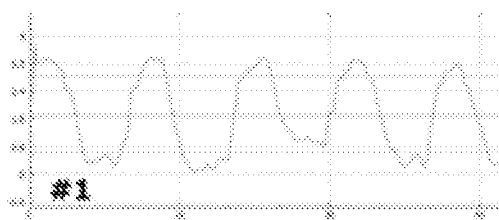 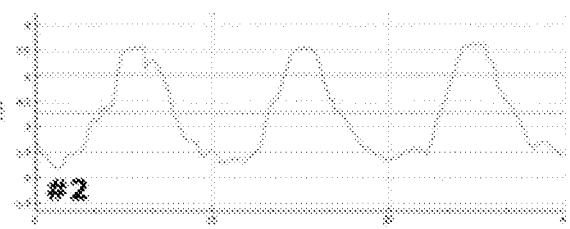
FIG. 3C             FIG. 3D

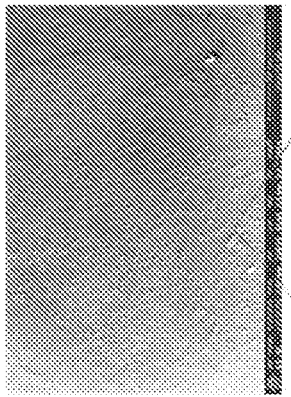
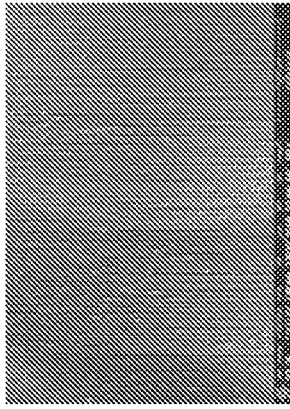
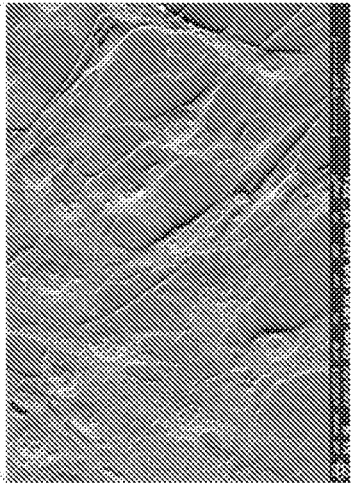
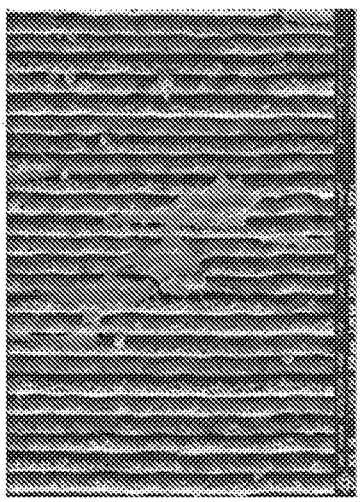
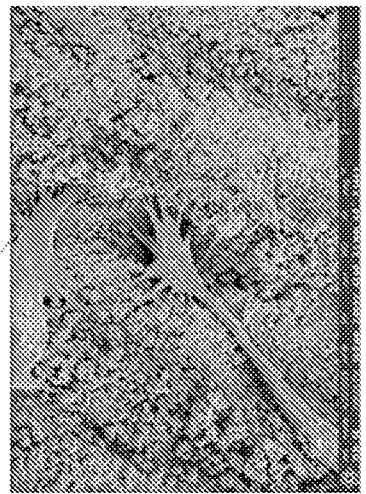

ALTERED MATERIAL MORPHOLOGY FOR REDUCING FIBROTIC LOAD, REDUCING NOISE AND IMPROVING EXTRACTABILITY OF IMPLANTABLE LEADS

FIELD

Embodiments relate to implantable-lead devices that include one or more materials with altered morphology and methods for making and using the same. Specifically, the morphology of electrodes and/or one or more other implant-device materials can be textured to include micro- and/or nanoscale topographical features, which can reduce in vivo fibrotic response and thereby improve signal-to-noise ratios and short-term extractability of the devices.

BACKGROUND

Medical implant devices are becoming more frequently used. However, a recurring issue is that the subject's body frequently exhibits undesired reactions to the device. For example, frequently an implant device can trigger an inflammatory response, which can result proliferation of fibroblasts. The fibroblast proliferation can result in fibrosis of nearby tissue, which can result in devascularization and scarring of the tissue. Thus, it would be desirable to identify techniques by which an implant device can be implanted without triggering a fibrotic response.

SUMMARY

In some embodiments, an implant device is provided that include one or more electrodes configured to receive and/or deliver electrical stimuli. The implant device can also include a biocompatible and flexible insulating material that is adjacent to or under at least one of the one or more electrodes. A surface of the biocompatible and flexible insulating material can include a pattern of a set of micron-scale or nanoscale features. A height of each of the set of micron-scale or nanoscale features can be between 1 nanometer and 100 microns such a thickness of the biocompatible and flexible insulating material is variable across at least a portion of the implant device.

In some instances, or each electrode of the one or more electrodes, another surface of the electrode includes another pattern of a second set of micron-scale or nanoscale features that result in variable thickness if the electrode across at least another portion of the implant device. The biocompatible and flexible insulating material may be in contact with at least a portion (e.g., a bottom and/or one or more or all sides) of each of the one or more electrodes. Each of the one or more electrodes can include a metal and/or metal alloy. The biocompatible and flexible insulating material can include a polymer, PEEK, a polyimide, polyurethane, liquid-crystal polymer or silicone and/or a copolymer. A height of each of the set of micron-scale or nanoscale features can be at least 1 micron. A height of each of the set of micron-scale or nanoscale features can be between 1 nanometer and 1 micron. A height of each of the set of micron-scale or nanoscale features can be between than 1 nanometer and 50 nanometers. The pattern can be configured such that thickness of the biocompatible and flexible insulating material along a dimension varies in accordance with a periodic pattern at least across a portion of the implant device. The variation of the thickness that is in accordance with the periodic pattern at least across a portion of the implant device can include at least two, at least five or at least ten cycles. The set of micron-scale or nanoscale features include a set of ridges extending along a dimension of the surface and/or a set of peaks.

In some instances, the implant device further includes a second biocompatible and flexible insulating material. A second surface of the second biocompatible and flexible insulating material can include a second pattern of a second set of micron-scale or nanoscale features that result in variable thickness of the second biocompatible and flexible insulating material. The surface of the biocompatible and flexible insulating material can be a top surface of the biocompatible and flexible insulating material, and the biocompatible and flexible insulating material can be positioned on the second biocompatible and flexible insulating material, such that a top surface of the second biocompatible and flexible insulating material is in contact with a bottom surface of the biocompatible and flexible insulating material. The second surface of the second of the biocompatible and flexible insulating material can be a bottom surface of the second of the biocompatible and flexible insulating material. Each of the biocompatible and flexible insulating material and the second biocompatible and flexible insulating material can include a thermoplastic LCP, and a melting point of the biocompatible and flexible insulating material can be different than a melting point of the second flexible and insulating material.

In some embodiments, a method of manufacturing an implant device is provided. One or more electrodes can be disposed on a biocompatible and flexible insulating layer. Each of the one or more electrodes can be configured to receive and/or deliver electrical stimuli. For each electrode of the one or more electrodes, an electrical connection can be formed between the electrode and a corresponding trace. The electrical connection can extend through at least part of the biocompatible and flexible insulating layer. A surface of the biocompatible and flexible insulating layer can be patterned to produce a set of micron-scale or nanoscale features on the surface. A height of each of the set of micron-scale or nanoscale features can be between 1 nanometer and 100 microns such a thickness of the biocompatible and flexible insulating layer is variable across at least a portion of the implant device.

In some embodiments, patterning the surface can include using nanoimprint lithography to form the micron-scale or nanoscale features. Patterning the surface can include using a micromolding technique to form the micron-scale or nanoscale features. The micron-scale or nanoscale features can be formed on one or more first portions of the surface, and the one or more electrodes can be disposed on one or more second portions of the surface. The method can further include disposing a first insulating material on a second biocompatible and flexible insulating layer, the disposed first insulating material layer forming the biocompatible and flexible insulating layer. The method can further include, for each electrode of the one or more electrodes, laser roughening an electrode surface of the electrode to produce another set of micron-scale or nanoscale features on the electrode surface, and a height of each of the other set of micron-scale or nanoscale features can be between 1 nanometer and 100 microns.

BRIEF DESCRIPTION OF THE DRAWINGS

Illustrative embodiments of the present invention are described in detail below with reference to the following drawing figures:

FIGS. 3A-3D illustrate topological features of a patterned surface according to an embodiment of the invention.

FIGS. 6A-6E show exemplary images of flat and roughened platinum iridium surfaces and fibroblast morphology on each of the surfaces.

DESCRIPTION

In some embodiments, techniques are provided for patterning one or more surfaces of an implant device. The patterning can be configured to result in formation of micron-scale or nanoscale features on the surface(s). The patterning can be performed using (for example) lithography, stamping, laser roughening or micro-molding. In some instances, a heating-lithography technique is performed to create a master mold (e.g., that includes inverse features), and a micro-molding technique is then performed using the master mold to form the features.

The implant device can include (for example) a device that includes one or more electrodes (e.g., for recording signals from one or more nerves or neurons and/or for delivering stimuli to one or more nerves or neurons). The implant device can further include one or more substrates (e.g., a flexible substrate) and/or other material(s) that may be positioned around and/or under the one or more substrates. The substrate(s) and/or material(s) can include an insulating material, such as silicone and/or a liquid-crystal polymer (LCP) (e.g., a thermoplastic LCP), a thermoplastic and/or a thermoset. An exemplary implant device can include a neural cuff that includes multiple electrodes and an insulating material, that is configured to be implanted to wrap around at least part of a nerve and that is configured to deliver stimuli at the multiple electrodes when implanted. One or more of the electrode(s), substrate(s) and/or material(s) can be patterned to produce the micron-scale or nanoscale features on the surface.

The patterning can inhibit fibroblasts from adhering to the device and impede proliferation of fibroblasts on the implant device, which can inhibit or delay a cascade of fibrous encapsulation (e.g., by inhibiting overproduction of extracellular matrix (ECM) proteins and implant fibrosis). In some instances, formation of a fibrous capsule around part or all of an implant device can be delayed by at least two or three weeks after implant. Inhibited proliferation of fibroblasts can also result in a reduction of noise in signals recorded by an implant device. The patterning can also inhibit differentiation of fibroblasts and alter protein adsorption (e.g., in a manner that results in inhibition of implant fibrosis). Further, the patterning can improve the extractability of the implant device, in that (for example) less force may be required to remove the implant device from a patient or site and/or in that removal of the device may be performed with less damage to surrounding tissues.

Figure 1A:
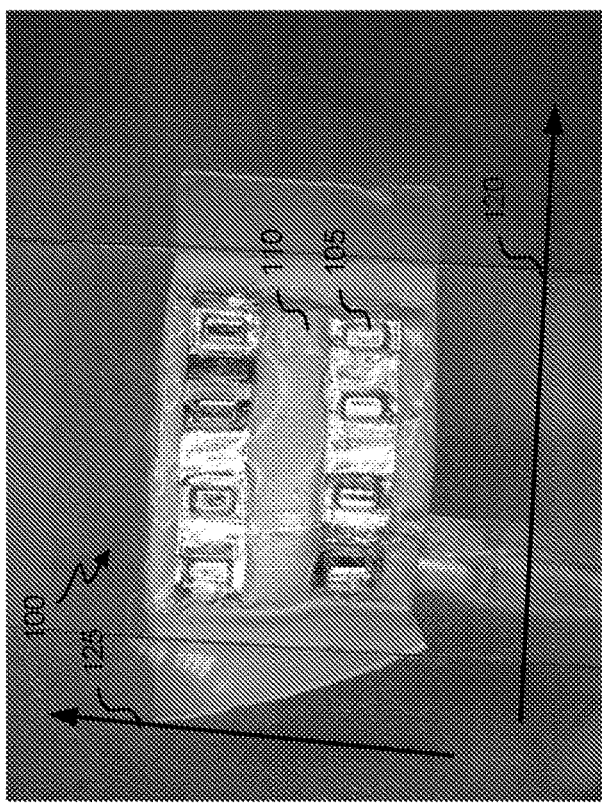
FIGS. 1A-1B show multiple views of an electrode cuff according to an embodiment of the invention.
Figure 1B:
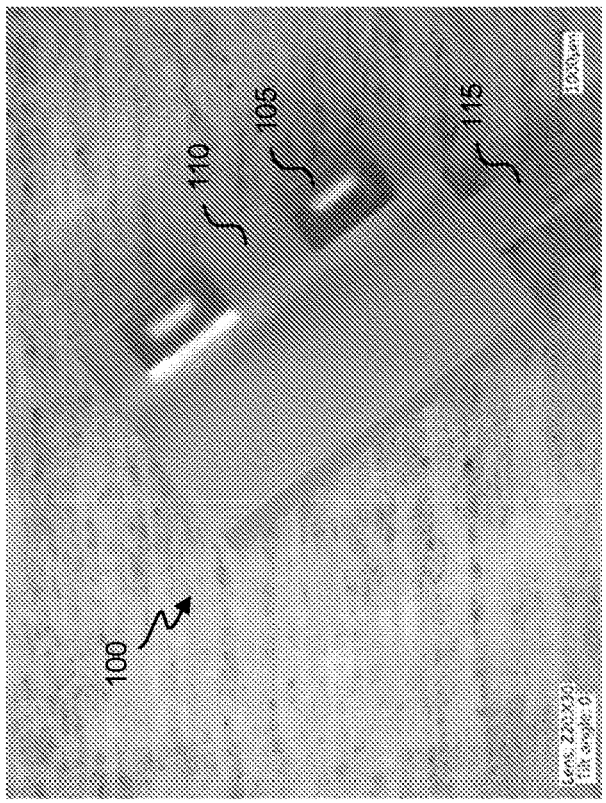

FIGS. 1A-1B show multiple views of an electrode cuff 100 according to an embodiment of the invention. Electrode cuff 100 can include a nerve cuff 100 that is configured to be implanted to at least partly wrap around part of a nerve (e.g., a peripheral nerve, such as the vagus nerve). FIG. 1A shows a first view in which electrode cuff 100 is closed, and FIG. 1B shows a second view in which electrode cuff 100 is unfurled. Electrode cuff 100 includes a set of electrodes 105 and an insulating material 110 (e.g., silicone). Each electrode 105 can be shaped, sized and/or configured to (for example) stimulate one or more particular compartments of a nerve that it is wrapped around (e.g., one or more nerve fibers, one or more nerve cells and/or one or more axons), stimulate the whole nerve that it is wrapped around, detect signals from one or more particular compartments of a nerve that it is wrapped around (e.g., one or more nerve fibers, one or more nerve cells and/or one or more axons), and/or detect signals from the whole nerve that it is wrapped around.

Insulating material 110 can be comprised of (for example) a thermoplastic material, an LCP, thermoplastic LCP and/or silicone. Insulating material 110 can be (for example) a thermoplastic substrate. Each of the set of electrodes 105 can be comprised of (for example) a metal, an alloy, platinum and/or platinum iridium. Each of the set of electrodes 105 can have (for example) a rectangular shape, though it will be appreciated that other shapes (e.g., circular, square, oval, etc.) are contemplated as well.

Each of one, more or all of the set of electrodes 105 can be electrically connected to a trace that extends away from electrode cuff 100 to connect with controlling electronics. In the depicted instances, all of the traces can extend from electrode cuff 100 within an insulating connector 115.

Electrode cuff 100 can be configured to have a width (along a first dimension 120) that is (for example) at least 0.5 mm, at least 1 mm, or at least 2 mm and/or that is (for example) less than 20 mm, less than 10 mm, or less than 5 mm. Electrode cuff 100 can be configured to have a length (along a second dimension 125) that is (for example) at least 5 mm, at least 10 mm, or at least 15 mm and/or that is (for example) less than 25 mm or less than 50 mm. Each electrode 105 can have a width (along first dimension 120) that is (for example) at least 0.05 mm, at least 0.1 mm, or at least 0.5 mm and/or that is (for example) less than 1 mm, less than 2 mm, or less than 5 mm. Each electrode 105 can have a length (along second dimension 125) that is (for example) at least 0.5 mm, at least 1 mm or at least 2 mm and/or that is (for example) less than 20 mm or less than 10 mm.

The set of electrodes 105 may be arranged to form multiple rows of electrodes 105, where each row includes a subset of the set of electrodes 105. In the depicted instance, each row includes four electrodes, though it will be appreciated that other quantities are contemplated. For example, each row may include at least 2, at least 3, or at least 5 electrodes and/or less than 5, less than 10, or less than 15 electrodes.

Electrode cuff 100 may be configured to curl along first dimension 120, such that electrode cuff 100 (and thus each row of electrodes) can at least partly wrap around a structure, such as a nerve. In some instances, electrode cuff 100 includes a curved shape and/or curved default shape. Electrode cuff 100 may be flexible to allow at least intermittent partial straightening of the cuff.

While not visible in FIG. 1A-1B, part or all of a surface of insulating material 110 and/or part or all of a surface each of one, some or all of the set of electrodes 105 can include a set of features that text the surface(s). Each of the set of features can have a height that is (for example) on a micron scale and/or on a nano scale. Each of the set of features can have a height that is (for example) at least 1 nm, at least 10 nm, at least 50 nm, at least 100 nm, at least 500 nm, at least 1 micron, at least 2 microns, at least 5 microns, or at least 10 microns. Each of the set of features can have a height that is (for example) less than 500 microns, less than 100 microns, less than 50 microns, less than 10 microns, less than 1 micron, less than 500 nm, less than 100 nm or less than 50 nm.

In some instances, each of the set of features has a high aspect ratio (e.g., a height-to-radius ratio that is at least 2:1, 3:1, 5:1 or 10:1). In some instances, a cross-sectional area of each of one, more or all of the features is not circular (or is not approximately circular). For example, a feature may include a thin ridge that runs across a portion of electrode cuff 100. A cross-sectional area of each feature can be characterized by a length along a first dimension and a width along a second dimension. The first dimension can be perpendicular to each of the second dimension and a vertical dimension, and the second dimension can be perpendicular to the vertical dimension. With respect to each of one, some or all features, the feature may be shaped such that a ratio of a height of the feature to a maximum and/or minimum of the first and second dimensions is at least 2:1, 3:1, 5:1 or 10:1.

Figure 2:
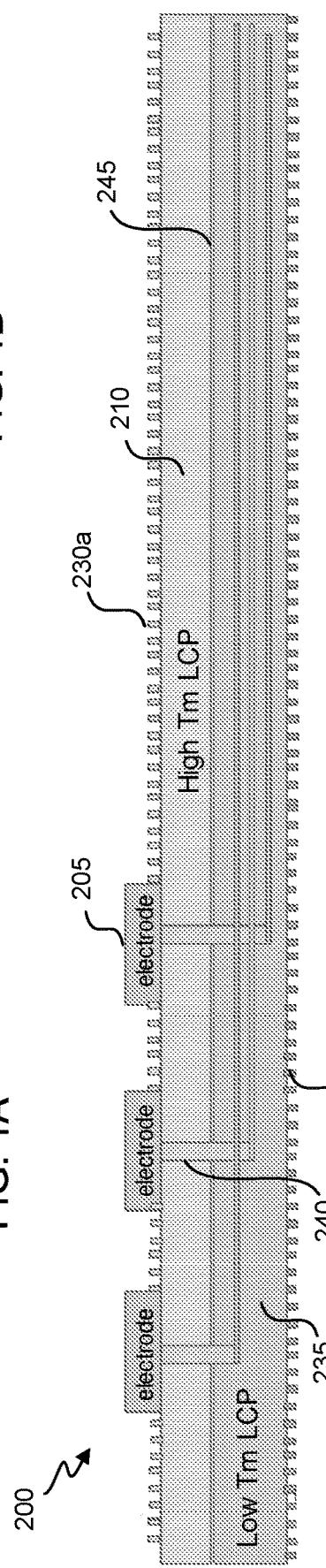
FIG. 2 shows a side-view depiction of a patterned electrode-cuff stack according to an embodiment of the invention.

FIG. 2 shows a side-view depiction of a patterned electrode-cuff stack 200 according to an embodiment of the invention. The depicted cross-section includes three electrodes 205, each of which may (for example) be associated with a different row or subset of electrodes. In the depicted instance, electrode-cuff stack 200 includes an insulating material comprising a high melting-point LCP 210, which is under and in contact with each electrode 205. High melting-point LCP 210 can have a melting temperature that is (for example) greater than 290° C., greater than 300° ° C., greater than 310° C., less than 400° C., less than 350° C., less than 320° C. and/or approximately 315° C.

A first set of micron-scale or nanoscale features 230a are on a top and/or outside surface of high melting-point LCP 210. First set of micron-scale or nanoscale features 230a may have been formed (for example) by stamping a top surface of high melting-point LCP 210 or using micromolding. As one example, electron beam lithography can be used to generate a micron- or nano-featured template mold in silicon or nickel that includes micron-scale or nanoscale features (e.g., having heights that are less than 50 nm, less than 20 nm or less than 10 nm). The mold can be placed in contact with a thermoplastic substrate (e.g., high melting-point LCP 210) that is to be patterned, and the temperature and pressure can be raised above the glass-transition temperature (Tg) and elastic modulus € of the thermoplastic (e.g., to permit reflowing of the thermoplastic). The temperature and pressure can then be returned to normal parameters, the patterned thermoplastic can be cured and the imprinted film can be released. As another example, a lamination technique can be employed using nanoporous aluminum oxide membranes as a nano-template. Heat and pressure can be applied to an LCP surface (e.g., of an LCP thin film) in contact with the aluminum oxide membrane. The membrane can then be dissolved (e.g., with a dilute sodium hydroxide solution).

Patterned electrode-cuff stack 200 includes a second insulating layer comprising a low melting-point LCP 235. Low melting-point LCP can have a melting temperature that is (for example) greater than 250° C., greater than 270° C., greater than 280° C., less than 310° C., less than 300° C. and/or approximately 290° C. A second set of micron-scale or nanoscale features 230b are on a bottom or outside surface of low melting-point LCP 230b. Second set of micron-scale or nanoscale features 230b may have been formed (for example) by stamping an exterior surface of low melting-point LCP 235 or using micromolding. In some instances, first set of micron-scale or nanoscale features 230a and second set of micron-scale or nanoscale features 230b may have similar or same shapes, cross-feature patterns, positions, dimensions, and/or aspect ratios. In some instances, first set of micron-scale or nanoscale features 230a have different shapes, cross-feature patterns, positions, dimensions and/or aspect ratios relative to second set of micron-scale or nanoscale features 230b.

Patterned electrode-cuff stack 200 includes a set of electrical vias 240 that connect each depicted electrode 205 to an electrical trace 245. Each electrode 205 can then receive stimulation parameters and/or stimulation commands through a corresponding electrical via 240 and electrical trace 245 and/or can transmit detected signals through a corresponding electrical via 240 and electrical trace 245. In some instances, a separate electrical via 240 and electrical trace 245 is connected to each electrode 205. In some instances, multiple electrodes 205 are electrically connected, such that an electrical via 240 may extend from one of the multiple electrodes 205, while other of the multiple electrodes 205 may not be directly connected to the via.

In use, an electrode-cuff device corresponding to patterned electrode-cuff stack 200 may be moved to a target location and oriented such that electrodes 205 are in contact with a nerve. Thus, at least some of first set of micron-scale or nanoscale features 230a may be in contact with the nerve. Second set of micron-scale or nanoscale features 230b may be in contact with surrounding biological material (e.g., surrounding tissue).

While not shown in FIG. 2, it will be appreciated that a top and/or exterior surface of electrodes 205 may further include a third set of micron-scale or nanoscale features. Depending on the embodiment, the third set of micron-scale or nanoscale features 230a have same or different shapes, cross-feature patterns, positions, dimensions and/or aspect ratios relative to first set of micron-scale or nanoscale features 230a and/or relative to second set of micron-scale or nanoscale features 230b. The third set of micron-scale or nanoscale features may be formed (for example) by laser roughening an exterior surface of the electrode(s) or using micromolding. In some instances, one or more micron-scale or nanoscale features can be formed using a technique as disclosed in U.S. Provisional Application 62/633,435, which is hereby incorporated by reference in its entirety for all purposes.

While FIGS. 1A, 1B and 2 relate to electrode-cuff devices, it will be appreciated that surfaces textured with micro- or nanoscale features (and techniques for making and/or using the same) can be used for other types of implant devices. For example, an implant device that includes an electrode array for recording neural activity may be configured to include micro- or nanoscale features. As other examples, an implant device (having a surface patterned to include micro- or nanoscale features) can include an implantable cardioverter defibrillator, an artificial hip, a heart pacemaker, a breast implant, spinal fusion hardware (e.g., a screw, rod and/or artificial disc), an intra-uterine device, fracture-repair hardware (e.g., a screw, pin, plate and/or rod), an artificial knee, a coronary stent, an ear tube or an artificial eye lens. In some instances, an implant device can include a device disclosed in or having features disclosed in U.S. application Ser. No. 15/597,187, which is hereby incorporated by reference in its entirety for all purposes. The features can mitigate a foreign-body response of a patient to implantation of the implant device, as the topographically variant features can inhibit fibrosis. For a recording implant device (e.g., that includes one or more electrodes), the features can reduce impedance (e.g., via a reduction of fibrosis).

One approach for inhibiting fibrosis is to coat a medical implant (e.g., with a hydrogel) to mitigate fibrotic response. In some instances, all or part of the implant device (e.g., any surface patterned with micron-scale or nanoscale features) lacks a coating (e.g., as the features themselves can mitigate a fibrotic response). The features can provide an approach for achieving a thin implant design (e.g., as the features can facilitate avoiding of an extra coating layer and also inhibit fibroblasts from adhering to the device and thus increasing a thickness), which can reduce impedance, improve device flexibility and improve signal-to-noise ratios.

FIGS. 3A-3D illustrate topological features of a patterned surface according to an embodiment of the invention. The depicted geometry of the features may correspond to geometry of features on a surface of an insulating layer, features on a surface of an electrode and/or features on another portion of an implant device. The features can include features resulting from a nanoimprint lithography performed using a mold (e.g., a mold made from e-beam lithography and/or a stainless-steel or nickel mold.

FIGS. 3A and 3B show two different view of a heat-map depiction of a height of a patterned surface. Dark red represents highest portions of the surface, while dark blue represents lowest portions of the surface. In this instance, each feature includes a peak or cone that is radially symmetric. The peak in the depicted instance includes a 6 µm diameter cone with a pitch of 10 µm. The features are positioned to be in a grid pattern, so as to form a set of rows and a set of columns of features, with the features being equally spaced across each row and each column.

FIGS. 3C and 3D show the spatially dependent height variation of the surface along the two lines shown in FIG. 3B. The y-value is defined such that zero corresponds to a minimum height across the surface. The cross-section represented in FIG. 3C is parallel to a row of features, while the cross-section represented in FIG. 3D is diagonal relative to rows of features. Thus, while the spatial height pattern represented in each of FIG. 3C and FIG. 3D are cyclical, the frequency of FIG. 3C is higher than the frequency of FIG. 3D, due to the orientation difference.

The spatial pattern shown in FIGS. 3C and 3D generally corresponds to a sinusoidal shape. It will be appreciated that other periodic patterns may instead be effected. For example, a cyclical variation of feature height may correspond to a square-wave shape or sawtooth wave and/or the spatial fluctuation may correspond to a clipped pattern (e.g., such that a top or bottom portion of a wave is pegged to a relative constant).

Inflammatory responses are often evoked in response to an implant device, which can result in proliferation of fibroblasts and impaired performance of the implant device. Patterning one or more surfaces of an implant device to produce micron-scale or nanoscale features can inhibit fibroblast proliferation (e.g., by at least two-fold or at least four-fold as compared to a comparable device with unpatterned surfaces).

Figure 4:
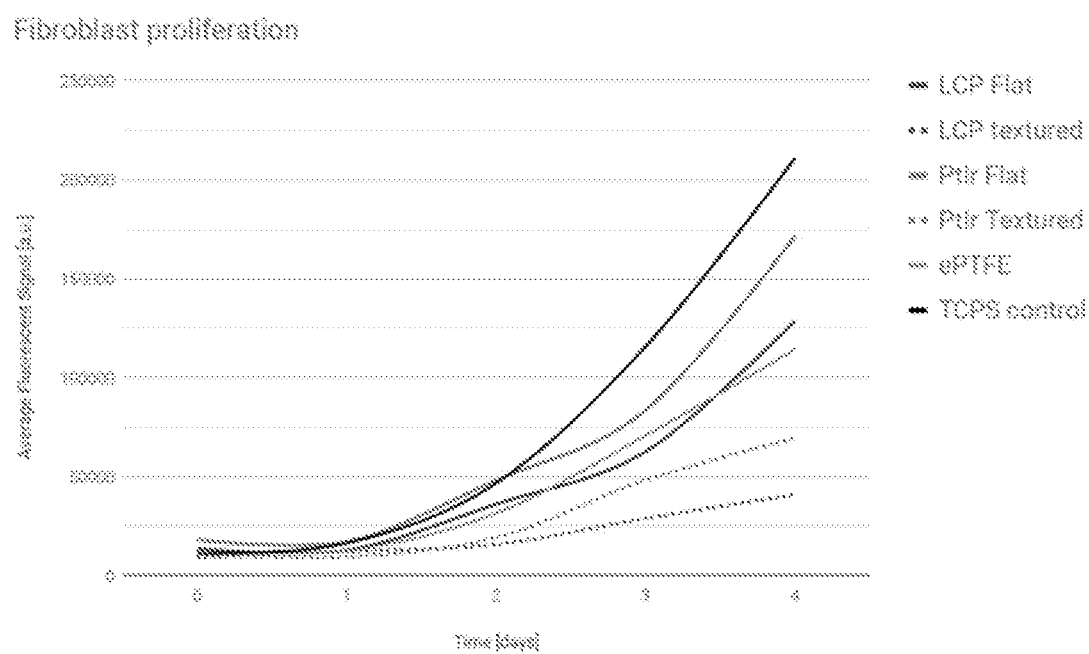
FIG. 4 shows a quantification of fibroblast proliferation across various types of surfaces according to an embodiment of the invention.

FIG. 4 shows a quantification of fibroblast proliferation across various types of surfaces according to an embodiment of the invention. Specifically, the curves show an extent to which fibroblasts proliferated over a four-day period on a flat LCP surface (lacking micron-scale or nanoscale features), a textured LCP surface (that—in the depicted instance—corresponds to a surface that includes micron-scale features), a flat platinum iridium (PtIr) surface (lacking micron-scale or nanoscale features), a textured PtIr surface (that includes micron-scale or nanoscale features), a flat expanded polytetrafluoroethylene (ePTFE) surface, and a flat tissue-culture polystyrene (TCPS) surface. ePTCE and TCPS are shown for comparison purposes. ePTFE is an FDA approved material that frequently is included in vascular grafts. The LCP surfaces represented in the data of FIG. 4 has a melting point between 200° C. and 240° C., which is lower than melting points of fluoro-polymers, while higher than melting points of thermoplastic polyurethanes.

For each data point and for each type of surface, six wells that included the corresponding type of surface as a substrate were assessed at the corresponding time point. Using a 6 mm biopsy punch, each type of surface was cut into a circular shape and glued to a bottom of a well plate using silastic adhesive. The wells were dried overnight. The films were disinfected with 70% EtOH overnight and air dried with UV exposure for at least thirty minutes.

At time-point zero, each well was seeded with 2000 fibroblasts. At the assessment time point, cell media was aspirated, and the well was frozen. CyQuant lysis buffer and a dye (nucleic acid binder) was used for quantification via fluorescence measurement. Each data point in FIG. 4 includes an average of the fluorescent signals collected using the corresponding six wells.

The plots in FIG. 4 shows that the two textured surfaces that include the micron-scale or nanoscale features were associated with the smallest degree of fibroblast proliferation across all of the surfaces. It will be appreciated that while the depicted data corresponds to a textured surface that includes micron-scale features, similar distinguishes between textured and flat surfaces expected when nano-scale features are used.

Figure 5A:
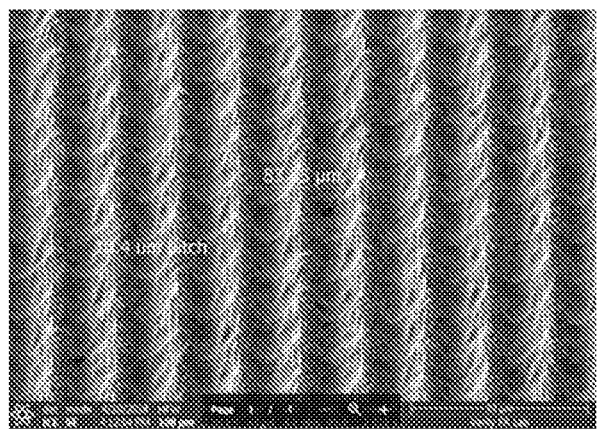
FIGS. 5A-5C show exemplary images of a nanoimprinted LCP surface and fibroblast morphology on each of flat LCP and the nanoimprinted LCP.
Figure 5B:
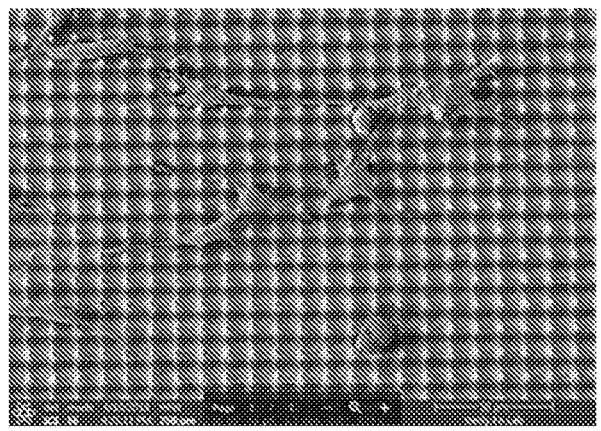
Figure 5C:
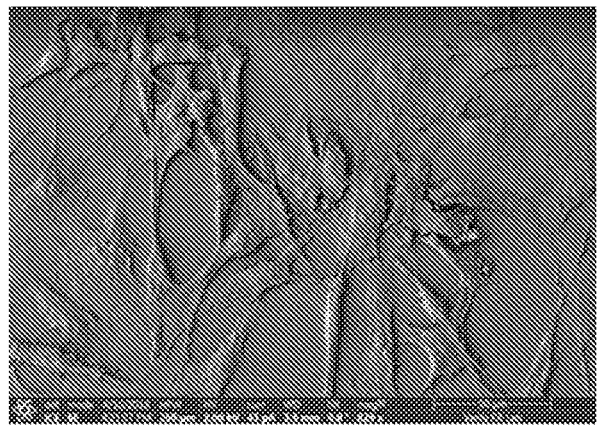

FIGS. 5A-5C show exemplary scanning electron microscopy (SEM) images of a nanoimprinted LCP surface and fibroblast morphology on each of flat LCP and the nanoimprinted LCP. FIG. 5A shows a patterned LCP surface formed by imprinting an LCP layer with a stainless steel stamp (e.g., under sufficiently high temperature and pressure conditions). In this instance, the pattern includes a set of peaks which are arranged in a grid structure. Separation between adjacent features within a row and within a column is approximately 11 µm. In this example, each peak is approximately 10 µm tall, with a 6 µm base diameter and 10 µm pitch.

FIG. 5B shows four-day fibroblast growth on the patterned surface of FIG. 5A. As shown, the fibroblasts are rounded and their growth is generally restricted to areas between the features, corresponding to unhealthy fibroblast morphology. The fibroblast growth on the patterned LCP surface of FIG. 5B can be compared to four-day fibroblast growth on a flat LCP surface, shown in FIG. 5C. The fibroblasts on the flat surface are larger and flatter, corresponding to a healthy morphology.

FIGS. 6A-6E show exemplary images of flat and roughened PtIr surfaces and fibroblast morphology on each of the surfaces. FIG. 6A shows a flat PtIr surface, while FIG. 6B shows a patterned PtIr surface. The patterned surface includes one generated via laser roughening of a PtIr surface (e.g., as described in U.S. Application No. 62/663,435, filed Apr. 27, 2018, which is hereby incorporated by reference in its entirety for all purposes. In this instance, the pattern includes a set of ridges, such that channels are formed between the ridges. The pattern can correspond to a 10 µm pitch.

FIG. 6C shows four-day fibroblast growth on the flat surface of FIG. 6A. The fibroblasts are dense, large and spread out, corresponding to a healthy morphology. FIGS. 6D and 6E show four-day fibroblast growth on the textured surface of FIG. 6B. The magnification of FIG. 6E is five times that of FIG. 6D and FIG. 6C, and the magnification of FIGS. 6C and 6D are the same. As compared to the flat-surface fibroblasts represented in FIG. 6C, the representations in FIGS. 6D and 6E indicate that the textured surface resulted in a lower density of fibroblasts. Further, for fibroblasts that have grown on the textured surface, the fibroblasts are rounder and more compact with stunted projections. The fibroblasts appear shown in FIG. 6D appear to be restrained by the channel topography and are aligned in the grooves. The features can thus provide topographical cues that influence where an extent to which fibroblasts grow.

FIGS. 5A-5C and 6A-6E thus illustrate that textured surfaces are associated with reducing fibroblast proliferation and further result in less healthy fibroblast morphologies. The presence and location of particular enzymes can further be indicative of an extent of fibroblast proliferation and can thus also be used as an indicator as to whether textured surfaces reduce fibroblast proliferation.

For example, focal adhesion kinase (FAK) is a transmembrane protein that mediates communication between a cell membrane. FAK is associated with signaling pathways for proliferation, migration and differentiation. FAK is specifically associated with cellular integrin-mediated signaling pathways, and integrins mediate cell proliferation through contact with ECM proteins and intracellular elements. When healthy fibroblasts are attached to a substrate and proliferating, FAK is present in a punctuated pattern at the periphery of the cell membrane, indicating adhesion to the underlying substrate.

FIGS. 7A-7D show exemplary immunofluorescence confocal microscopy images for which focal adhesion kinase (FAK) is labeled. Specifically, wells were fitted with substrates and seeded with fibroblasts as described with respect to FIG. 4. After four days from seeding, stains were applied such that FAK is labeled in red, and F-actin (that corresponds to cells' cytoplasms) is labeled in green, and cells' nuclei are labeled in blue. Specifically, a blocking solution was made using 5% BSA, 2% goat serum, 0.1% Tween 20, and 0.1% TritonX100. Further, antibody serial dilutions were made using the blocking solution and corresponding antibodies.

Cells were fixed with 4% paraformaldehyde for 15 minutes and then rinsed with PBS. 100 µL of blocking solution was added to each of the wells. 30-60 minutes after the blocking solution was added, the wells were washed three times with PBS-T, with each rinse being for five minutes. Antibodies were combined with the blocking solution (e.g., in a 1:50 ratio for the FAK staining and F-actin and a 1:20 staining for the cells' nucleus staining). The wells were then washed for 5 minutes in 1 mL PBS and mounted to glass slides with mounting media for imaging.

Figure 7A:
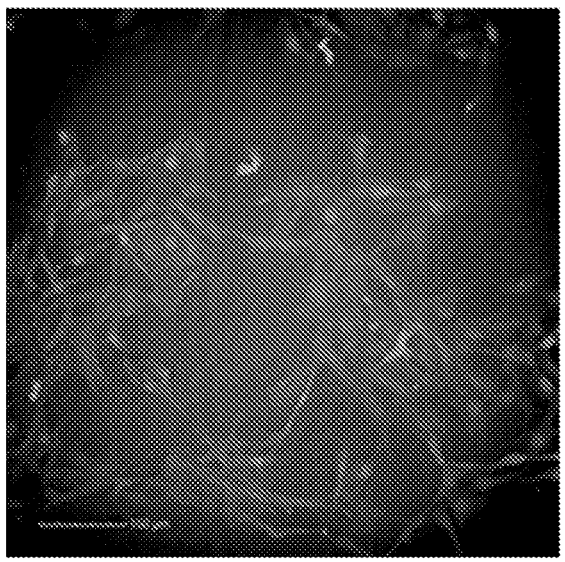
FIGS. 7A-7D show exemplary immunofluorescence confocal microscopy images for which focal adhesion kinase (FAK) is labeled.
Figure 7B:
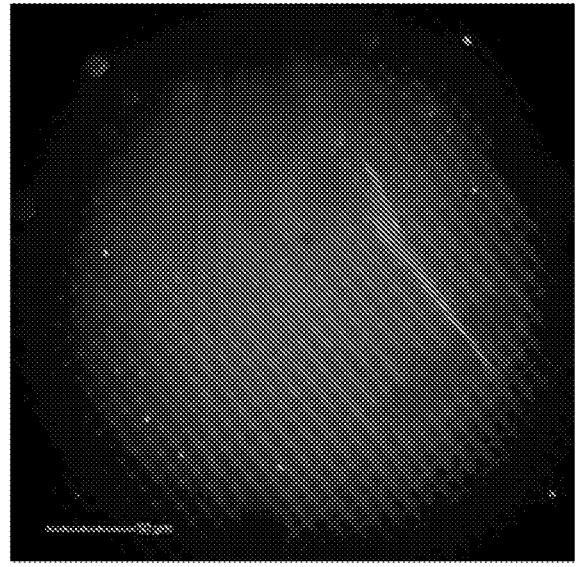
Figure 7C:
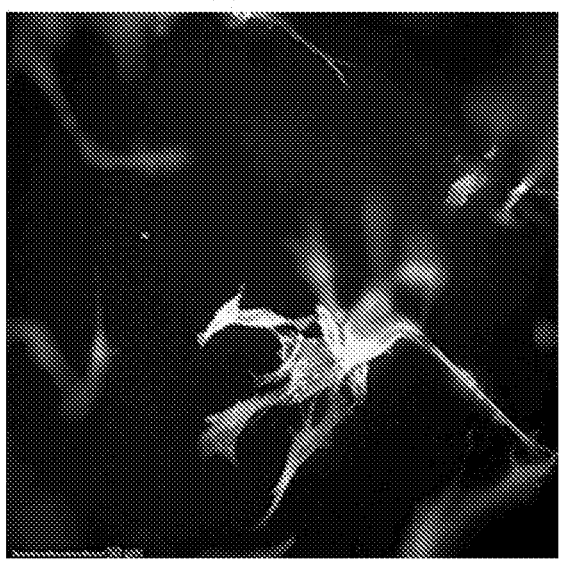
Figure 7D:
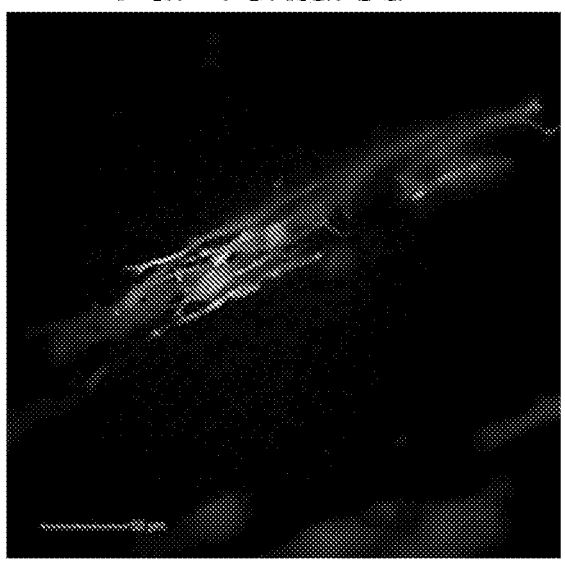

FIGS. 7A and 7B correspond to an LCP surface, and FIGS. 7C and 7D correspond to a PtIr surface. The surfaces of FIGS. 7A and 7C are flat, while the surfaces of FIGS. 7B and 7D are textured with features. Each textured surface included a set of cone features. Each cone had an approximate height of 10 µm, base diameter of 6 µm, and pitch of 7 µm. The cones were randomly oriented and quasi-periodical across the surface, with a spike-to-spike distance of 7 µm.

As shown, with respect to the flat surfaces, FAK is present at the edges of the projections. Further, the cytoplasms are widespread. Meanwhile, for the textured surfaces, FAK is clustered by the fibroblasts' nuclei, and the cytoplasms are compact. Thus, the images indicate that the fibroblasts that do attach to a textured surface are not as effective at promoting fibroblast proliferation as compared to fibroblasts that attach to a flat surface.

Specific details are given in the above description to provide a thorough understanding of the embodiments. However, it is understood that the embodiments can be practiced without these specific details. For example, circuits can be shown in block diagrams in order not to obscure the embodiments in unnecessary detail. In other instances, well-known circuits, processes, algorithms, structures, and techniques can be shown without unnecessary detail in order to avoid obscuring the embodiments.

It is noted that the embodiments can be described as a process which is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. A process is terminated when its operations are completed, but could have additional steps not included in the figure.

While the principles of the disclosure have been described above in connection with specific apparatuses and methods, it is to be clearly understood that this description is made only by way of example and not as limitation on the scope of the disclosure.

What is claimed is:

1. An implant device comprising:
   one or more electrodes configured to receive or deliver electrical stimuli; and
   a biocompatible and flexible insulating material that is adjacent to or under at least one of the one or more electrodes, wherein a surface of the biocompatible and flexible insulating material comprises a pattern of a set of micron-scale or nanoscale features, and wherein a height of each of the set of micron-scale or nanoscale features is between 1 nanometer and 100 microns such that a thickness of the biocompatible and flexible insulating material is variable across at least a portion of the implant device,
   wherein, for each electrode of the one or more electrodes, another surface of the electrode comprises another pattern of a second set of micron-scale or nanoscale features that result in variable thickness of the electrode across at least another portion of the implant device, and
   wherein the set of micron-scale or nanoscale features are formed on the surfaces with micron-scale or nanoscale feature molds generated using electron-beam lithography.

2. The implant device of claim 1, wherein the biocompatible and flexible insulating material is in contact with at least a portion of each of the one or more electrodes.

3. The implant device of claim 1, wherein each of the one or more electrodes includes a metal or metal alloy.

4. The implant device of claim 1, wherein the biocompatible and flexible insulating material includes a polymer.

5. The implant device of claim 1, wherein a height of each of the set of micron-scale or nanoscale features is at least 1 micron.

6. The implant device of claim 1, wherein a height of each of the set of micron-scale or nanoscale features is between 1 nanometer and 1 micron.

7. The implant device of claim 1, wherein a height of each of the set of micron-scale or nanoscale features is between than 1 nanometer and 50 nanometers.

8. The implant device of claim 1, wherein the pattern is configured such that thickness of the biocompatible and flexible insulating material along a dimension varies in accordance with a periodic pattern at least across a portion of the implant device, and wherein the variation of the thickness that is in accordance with the periodic pattern at least across a portion of the implant device includes at least five cycles.

9. The implant device of claim 1, further comprising:
a second biocompatible and flexible insulating material, wherein a second surface of the second biocompatible and flexible insulating material comprises a second pattern of a second set of micron-scale or nanoscale features that result in variable thickness of the second biocompatible and flexible insulating material.

10. The implant device of claim 9, wherein:
the surface of the biocompatible and flexible insulating material is a top surface of the biocompatible and flexible insulating material;
the biocompatible and flexible insulating material is positioned on the second biocompatible and flexible insulating material, such that a top surface of the second biocompatible and flexible insulating material is in contact with a bottom surface of the biocompatible and flexible insulating material; and
the second surface of the second of the biocompatible and flexible insulating material is a bottom surface of the second of the biocompatible and flexible insulating material.

11. The implant device of claim 9, wherein each of the biocompatible and flexible insulating material and the second biocompatible and flexible insulating material comprises a thermoplastic liquid-crystal polymer (LCP), and wherein a melting point of the biocompatible and flexible insulating material is different than a melting point of the second flexible and insulating material.

12. The implant device of claim 1, wherein the set of micron-scale or nanoscale features include a set of ridges extending along a dimension of the surface.

13. The implant device of claim 1, wherein the set of micron-scale or nanoscale features include a set of peaks.

14. A method of manufacturing an implant device, the method comprising:
disposing one or more electrodes on a biocompatible and flexible insulating layer, wherein each of the one or more electrodes is configured to receive or deliver electrical stimuli;
forming, for each electrode of the one or more electrodes, an electrical connection between the electrode and a corresponding trace, the electrical connection extending through at least part of the biocompatible and flexible insulating layer; and
patterning a surface of the biocompatible and flexible insulating layer to produce a set of micron-scale or nanoscale features on the surface, wherein a height of each of the set of micron-scale or nanoscale features is between 1 nanometer and 100 microns such that a thickness of the biocompatible and flexible insulating layer is variable across at least a portion of the implant device,
wherein, for each electrode of the one or more electrodes, another surface of the electrode comprises another pattern of a second set of micron-scale or nanoscale features that result in variable thickness of the electrode across at least another portion of the implant device, and
wherein the set of micron-scale or nanoscale features are formed on the surfaces with micron-scale or nanoscale feature molds generated using electron-beam lithography.

15. The method of claim 14, wherein patterning the surface includes using nanoimprint lithography to form the micron-scale or nanoscale features.

16. The method of claim 14, wherein patterning the surface includes using a micromolding technique to form the micron-scale or nanoscale features.

17. The method of claim 14, wherein the micron-scale or nanoscale features are formed on one or more first portions of the surface, and wherein the one or more electrodes are disposed on one or more second portions of the surface.

18. The method of claim 14, further comprising:
disposing a first insulating material on a second biocompatible and flexible insulating layer, wherein the disposed first insulating material layer forms the biocompatible and flexible insulating layer.

19. The method of claim 14, further comprising, for each electrode of the one or more electrodes:
laser roughening an electrode surface of the electrode to produce another set of micron-scale or nanoscale features on the electrode surface, wherein a height of each of the other set of micron-scale or nanoscale features is between 1 nanometer and 100 microns.

* * * * *